(12) United States Patent
Simpson et al.

(10) Patent No.: US 8,383,803 B2
(45) Date of Patent: Feb. 26, 2013

(54) PITX3 EXPRESSION PROMOTERS

(75) Inventors: Elizabeth M. Simpson, Vancouver (CA); Wyeth W. Wasserman, Vancouver (CA); Robert A. Holt, North Vancouver (CA); Steven J. Jones, Burnaby (CA); Daniel Goldowitz, Memphis, TN (US); Elodie Portales-Casamar, Vancouver (CA); Cletus D'Souza, Vancouver (CA); Vikramjit Chopra, Vancouver (CA)

(73) Assignee: The University of British Columbia (CA)

( * ) Notice: Subject to any disclaimer, the term of this patent is extended or adjusted under 35 U.S.C. 154(b) by 21 days.

(21) Appl. No.: 12/538,771

(22) Filed: Aug. 10, 2009

(65) Prior Publication Data

US 2010/0129903 A1    May 27, 2010

Related U.S. Application Data

(60) Provisional application No. 61/136,084, filed on Aug. 11, 2008.

(51) Int. Cl.
*C07H 21/04* (2006.01)
*C12N 15/63* (2006.01)
*A01K 67/00* (2006.01)

(52) U.S. Cl. ............... 536/24.1; 435/320.1; 435/455

(58) Field of Classification Search .................. None
See application file for complete search history.

(56) References Cited

FOREIGN PATENT DOCUMENTS

WO    WO 2007/003397    *    1/2007

OTHER PUBLICATIONS

Semina et al. Identification of promoter and other regulatory regions of Pitx3 gene. Invest. Ophthalmol. Vis. Sci. 44: e-Abstract 418, 2003.*
Attwood, T.K. The Babel of Bioinformatics. Science 290:471-473, 2000.*
Kyrpides et al. Whole-genome sequence annotation: "Going wrong with confidence". Mol. Microbiology 32:886-887, 1999.*
Gerhold et al. It's the genes! EST access to human genome content. BioEssays 18:973-981, 1996.*
Alam et al. Lung surfactant protein B promoter function is dependent on the helical phasing, orientation and combinatorial actions of cis-DNA elements. Gene 182:103-111, 2002.*
Muller et al. Repression of lac promoter as a function of distance, phase and quality of an auxiliary lac operator. J. Mol. Biol. 257:21-29, 1996.*
Xie et al. Domains of the rat rDNA promoter must be aligned stereospecifically. Molecular and Cellular Biology 12:1266-1275, 1992.*
Castillo-Carranza; et al., "Pitx3 promoter directs Cre-recombinase specifically in a human neuroblastoma cell line", Mol Cell Biochem (2008), 309(1-2):223-7.
Coulon; et al., "A Muscle-specific Promoter Directs Pitx3 Gene Expression in Skeletal Muscle Cells", The Journal of Biological Chemistry (2007), 282(45):33192-33200.
Korotkova; et al., "Differential expression of the homeobox gene Pitx3 in midbrain dopaminergic neurons", Eur J Neurosci (2005), 22(6):1287-93.
Rieger; et al., "A double-deletion mutation in the Pitx3 gene causes arrested lens development in aphakia mice", Genomics (2001), 72(1):61-72.
Smidt; et al., "Homeobox gene Pitx3 and its role in the development of dopamine neurons of the substantia nigra", Cell Tissue Res (2004), 318(1):35-43.

* cited by examiner

*Primary Examiner* — Quang Nguyen
(74) *Attorney, Agent, or Firm* — Bozicevic, Field & Francis LLP; Pamela J. Sherwood

(57) ABSTRACT

Isolated polynucleotides comprising a PITX3 promoter are provided, where a PITX3 regulatory element is operably joined to a PITX3 basal promoter utilizing a non-native spacing between the promoter and regulatory elements. The promoter may be operably linked to an expressible sequence, e.g. reporter genes, genes encoding a polypeptide of interest, regulatory RNA sequences such as miRNA, siRNA, antisense RNA, etc., and the like. In some embodiments a cell comprising a stable integrant of an expression vector is provided, which may be integrated in the genome of the cell. The promoter may also be provided in a vector, for example in combination with an expressible sequence. The polynucleotides find use in a method of expressing a sequence of interest, e.g. for identifying or labeling cells, monitoring or tracking the expression of cells, etc.

7 Claims, 4 Drawing Sheets

Figure 1:
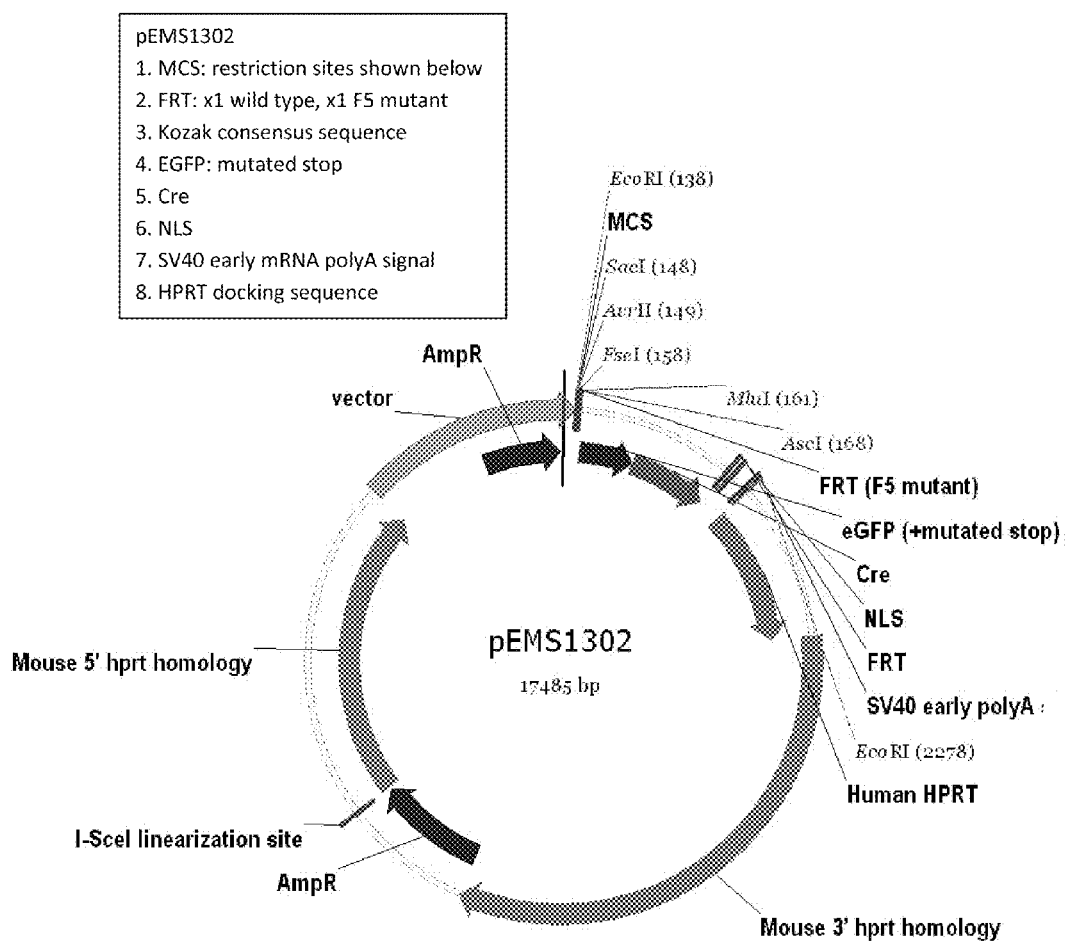

A.

Human_chr10: 10399189901-103991766 (reverse complement)

Conservation profile

B.

Human_chr10: 103983533-103986500 (reverse complement)

Conservation profile

```
                          SEQUENCE LISTING

<160> NUMBER OF SEQ ID NOS: 3

<210> SEQ ID NO 1
<211> LENGTH: 3639
<212> TYPE: DNA
<213> ORGANISM: Homo sapiens

<400> SEQUENCE: 1
cgattgtggg ctctcactat gtccctggtc tacctctctg gcttcaggac ttaagtgggt      60
ccacatgaca gctgacttat tgccatgggg ttgtgtctct tggaaaccat ggcctcccca     120
ctgtggcctc cctggcctgg gatctgctct ccaccttcat atgtcctgga tatttcattc     180
ttgctgcagt ccatgaccag gcttcctgta attccagcct gtactacaga atcagagcat     240
acctgtaggc cctctgtact ccctgggcct gggattgcca ccctgatacc agtgggactg     300
ggccacacat ccctcacatc cctagcaggg tgtggcaaaa agtctagggg tggggccggc     360
agcccccttc cagagctgga ctcaccatca ctgttatctt ctgactctct ctgtccctgc     420
ctgggcattt cttactagca tcaaccaatc ctgcggcttc cagacctact gcttgttctt     480
ccctatccac tgagtgaggc gaagtccctg gcctcagtcc caactcccta gcttcctgac     540
ctccagcagt ttgggggagc ttaatcttca gccagcctgt ctccagctca gacaacagct     600
tggcgccccc agcctttgcc tgaccagccc acccggacgt gagtcggcta gaggtctatg     660
cccccaccct tccatctctc tattgcctgc ctggctttac tgttctttcc ttctctcttc     720
agtttcacgg tcaggtccct tctcagctgt ggctcctctc tctgctgtta ctagcccatg     780
caagagccta aaggcttcat tctttcctct accagtccct tgtcccccaaa gtggctccca     840
```

-continued

```
gcttgggtta ctctgcccat tttgctgtta ccttgttgac tgggtcacct atgctcagga      900
cagagtgttc acagcatgtg ttgcctatct ctcagtaatg cagcgtactc accttcattc      960
accagggaaa cacttcactg gaggatacag agtctgggca gatgactcac tcaaggaagg     1020
gcagacacag ggatgagatc ttagccacca ctccaccctc agtgcctaac tcaatgccca     1080
gctcatagaa tgtgctaaat aaacatttgt ttaatgagtg aggaaaaaaa actactcagg     1140
tagagtttta tccctactca tatttacatg tttatgtttt tatctaaacc ttataacaac     1200
actgaaggca agtagggaag ggatcatgaa cttcctttcg gagatgaaga aatgtgctca     1260
gagaggtaaa gtaacttgcc gaggacacac agctagtaag ttgtacagcc aggacgtgaa     1320
tctagatctg ctgactctaa acctaatttc tttgggctat accagatgac tttcctgaga     1380
ggggcctggg cactttctgc ccctcctccc caccccatcc tctagctcca gcattctcat     1440
gccttctcct cactcagcag catccagtgc agaacactcc cctggcccct tggcctgctc     1500
ctcccccaca cagagtcctt agctcctggg actgagagct gaggttcaga ggggccaggg     1560
aggcggtggg ggggggggggg tgggtggggg aagggtaata atggctagct ccaaaacagc     1620
cccggcagct gtccctgtca cagagaggag actgtgtgac ggtacgtgtc tgtctgcctg     1680
gatgtggcag cgcatgtgtg ggagagtgtg tgtttgtgtg cccctagctc caagtccaag     1740
tgcttattat gtctgagtgg gggcctgtgt gtgtctgcac atgtgtctgt ctgtctctgg     1800
gaacacgcag cctgaactcg gctttctggc ctcggctttt cctcgcccat atcccttctc     1860
accctgcctc cctctgctga aataaagtga aagcaagatg caggtatgga atgccgggga     1920
cagggtaatt tggaaaactg caagtcggga gccaaagctg actggaaggc taggtggcaa     1980
gggtgggact gcttttccca caggtaaacc cctctctggg tttttttccca gctccatgtt     2040 gcttccatgg cctctggaaa agtcagggg atgatttgca tttcaaggc atcttgggta      2100 tgaagtaagg ggtatgaagt aaggggagac ttcagagcac ccctttttcc aactctcagt     2160 tctaacccctt cctccctcat cttcccagcc aaggctacca tagttccttc tcagggacat     2220 ctccccttcca tcagagcatt gttggccaaa gttttccagc tccaaacccc ctgacctgac     2280
ccgacctgga aggggaagta agctgagcac acctccagtt ctggcctgac tttttctcctg     2340 tcctgggttc cctccagccc tgtctcttca cacccaataa aaggtccaag atctagaccc     2400
ctctgcctgt ggaaagagca gggactcttt ctcaacctcc tgccttgacc tcggttccac     2460
tcccaacctg gcttgagagg tggggtgggg agtgggggca cagctgtgat ctctgagctg     2520 ttgaagggggg cattaccatg tgcaaataca ggctgctgcc catctgcacc tccctgagaa     2580
aggctcctaa taaatccaga gcagccaagt gacacacatc tcaatctagg ctaatccacc     2640
acattaatgc catcctgtgc agcctgcatt aagcccctgt taatgggggaa ggggtgagag     2700 aggcagagag gcccctccca ctcagctctc tacccccttcc ctctgtccct agcctccttc     2760
tgttctcctc caaccaaaag gcacccagag tcttgagccc cagtattgcc catttccctt     2820
cctcccagca gaggggtcct gggagagcag gcagaaaagg ggaccctgcg ggggaaactt     2880
ggagaaggac cctgggaggc tcctgggcaa tgtgaggcta agtttgggaa aggaagtatg     2940
agtaggaagg tggtctaatg aagctcctgc cggaggatt ggaacagaga caaaagggag      3000
gagagacgga cagcgacaag tggagaaaat cggcgaaact tgagtggcag agaagtctga     3060
gcgctgagac ccggcggccc cgtgcgcctt cccacctggc gccgatccac tttcctcggg     3120
gtagcggccc aacccacttc gctgccagcc gatcccttt acccgtggct accgggacca      3180
ctctactctc gcccacttgg ctctgcctaa gcgtcctagc cggagcgcgg tctctgccac     3240
```

-continued

| | | | | |
|---|---|---|---|---|
| gtggggaggg | gcgcggccga | gttgctgaag | agcgcttctg | attggccaga | gggcggggtt | 3300 |
| cttggcgtct | cgccgccag | acccctccct | caaaggcggg | gcctggagat | ccacagctgg | 3360 |
| aaagggcgga | gccccagcag | ggcagctgga | aagggcggg | gcctgacgcg | cgcggctcgc | 3420 |
| cgcggcgggc | tgggggcgcc | ctggtctgcc | ataaagtgaa | tgggcgcgg | ctgggggtgg | 3480 |
| cagtacgcgg | tgaggctcac | tccctccgag | agtccaggag | cgcccgagcg | gagaggcggc | 3540 |
| ccgggagcag | gggggcggcc | cccactccgg | ccgggtgccc | ggcccctggc | ccctgcctgc | 3600 |
| cctctagatc | gccgccgcag | ccgccgctac | tgggagtct | | | 3639 |

<210> SEQ ID NO 2
<211> LENGTH: 2971
<212> TYPE: DNA
<213> ORGANISM: Homo sapiens

<400> SEQUENCE: 2

| | | | | | |
|---|---|---|---|---|---|---|
| cgattgtggg | ctctcactat | gtccctggtc | tacctctctg | gcttcaggac | ttaagtgggt | 60 |
| ccacatgaca | gctgacttat | tgccatgggg | ttgtgtctct | tggaaaccat | ggcctcccca | 120 |
| ctgtggcctc | cctggcctgg | gatctgctct | ccaccttcat | atgtcctgga | tatttcattc | 180 |
| ttgctgcagt | ccatgaccag | gcttcctgta | attccagcct | gtactacaga | atcagagcat | 240 |
| acctgtaggc | cctctgtact | ccctgggcct | gggattgcca | ccctgatacc | agtgggactg | 300 |
| ggccacacat | ccctcacatc | cctagcaggg | tgtggcaaaa | agtctagggg | tggggccggc | 360 |
| agcccccttc | cagagctgga | ctcaccatca | ctgttatctt | ctgactctct | ctgtccctgc | 420 |
| ctgggcattt | cttactagca | tcaaccaatc | ctgcggcttc | cagacctact | gcttgttctt | 480 |
| ccctatccac | tgagtgaggc | gaagtccctg | gcctcagtcc | caactcccta | gcttcctgac | 540 |
| ctccagcagt | ttgggggagc | ttaatcttca | gccagcctgt | ctccagctca | gacaacagct | 600 |
| tggcgccccc | agcctttgcc | tgaccagccc | accggacgt | gagtcggcta | gaggtctatg | 660 |
| cccccaccct | tccatctctc | tattgcctgc | ctggctttac | tgttctttcc | ttctctcttc | 720 |
| agtttcacgg | tcaggtccct | tctcagctgt | ggctcctctc | tctgctgtta | ctagcccatg | 780 |
| caagagccta | aaggcttcat | tcttttcctct | accagtccct | tgtccccaaa | gtggctccca | 840 |
| gcttgggtta | ctctgcccat | tttgctgtta | ccttgttgac | tgggtcacct | atgctcagga | 900 |
| cagagtgttc | acagcatgtg | ttgcctatct | ctcagtaatg | cagcgtactc | accttcattc | 960 |
| accagggaaa | cacttcactg | gaggatacag | agtctgggca | gatgactcac | tcaaggaagg | 1020 |
| gcagacacag | ggatgagatc | ttagccacca | ctccacccctc | agtgcctaac | tcaatgccca | 1080 |
| gctcatagaa | tgtgctaaat | aaacatttgt | ttaatgagtg | aggaaaaaaa | actactcagg | 1140 |
| tagagtttta | tccctactca | tatttacatg | tttatgtttt | tatctaaacc | ttataacaac | 1200 |
| actgaaggca | agtagggaag | ggatcatgaa | cttccttcg | gagatgaaga | aatgtgctca | 1260 |
| gagaggtaaa | gtaacttgcc | gaggacacac | agctagtaag | ttgtacagcc | aggacgtgaa | 1320 |
| tctagatctg | ctgactctaa | acctaatttc | tttgggctat | accagatgac | tttcctgaga | 1380 |
| ggggcctggg | cactttctgc | ccctcctccc | caccccatcc | tctagctcca | gcattctcat | 1440 |
| gccttctcct | cactcagcag | catccagtgc | agaacactcc | cctggcccct | tggcctgctc | 1500 |
| ctcccccaca | cagagtcctt | agctcctggg | actgagagct | gaggttcaga | ggggccaggg | 1560 |
| aggcggtggg | gggggggggg | tgggtggggg | aagggtaata | atggctagct | ccaaaacagc | 1620 |
| cccggcagct | gtccctgtca | cagagaggag | actgtgtgac | ggtacgtgtc | tgtctgcctg | 1680 |
| gatgtggcag | cgcatgtgtg | ggagagtgtg | tgtttgtgtg | ccctagctc | caagtccaag | 1740 |

-continued

```
tgcttattat gtctgagtgg gggcctgtgt gtgtctgcac atgtgtctgt ctgtctctgg   1800
gaacacgcag cctgaactcg gctttctggc ctcggctttt cctcgcccat atcccttctc   1860
accctgcctc cctctgctga ataaagtgaa aagcaagatg caggtatgga atgccgggga   1920
cagggtaatt tggaaaactg caagtcggga gccaaagctg actggaaggc taggtggcaa   1980
gggtgggact gcttttccca caggtaaacc cctctctggg ttttttccca gctccatgtt   2040
gcttccatgg cctctggaaa agtcaggggg atgatttgca tttcaagggc atcttgggta   2100
tgaagtaagg ggtatgaagt aaggggagac ttcagagcac cccttttcc aactctcagt    2160 tctaacccttt cctccctcat cttcccagcc aaggctacca tagttccttc tcagggacat   2220
ctcccttcca tcagagcatt gttggccaaa gttttccagc tccaaacccc ctgacctgac   2280
ccgacctgga aggggaagta agctgagcac acctccagtt ctggcctgac ttttctcctg   2340
tcctgggttc cctccagccc tgtctcttca cacccaataa aaggtccaag atctagaccc   2400
ctctgcctgt ggaaagagca gggactcttt ctcaacctcc tgccttgacc tcggttccac   2460
tcccaacctg gcttgagagg tggggtgggg agtgggggca cagctgtgat ctctgagctg   2520
ttgaaggggg cattaccatg tgcaaataca ggctgctgcc catctgcacc tccctgagaa   2580
aggctcctaa taaatccaga gcagccaagt gacacacatc tcaatctagg ctaatccacc   2640
acattaatgc catcctgtgc agcctgcatt aagcccctgt taatggggaa ggggtgagag   2700
aggcagagag gcccctccca ctcagctctc tacccttcc ctctgtccct agcctccttc    2760
tgttctcctc caaccaaaag gcacccgag tcttgagccc cagtattgcc catttccctt    2820
cctcccagca gaggggtcct gggagagcag gcagaaaagg ggaccctgcg ggggaaactt   2880
ggagaaggac cctgggaggc tcctgggcaa tgtgaggcta gtttgggaa aggaagtatg    2940 agtaggaagg tggtctaatg aagctcctgc c                                  2971
```

<210> SEQ ID NO 3
<211> LENGTH: 668
<212> TYPE: DNA
<213> ORGANISM: Homo sapiens

<400> SEQUENCE: 3

```
gggaggattg gaacagagac aaaagggagg agagacggac agcgacaagt ggagaaaatc     60
ggcgaaactt gagtggcaga gaagtctgag cgctgagacc cggcggcccc gtgcgccttc    120
ccacctggcg ccgatccact ttcctcgggg tagcggccca acccacttcg ctgccagccg    180
atccctttta cccgtggcta ccgggaccac tctactctcg cccacttggc tctgcctaag    240
cgtcctagcc ggagcgcggt ctctgccacg tggggagggg cgcggccgag ttgctgaaga    300
gcgcttctga ttggcagag gcggggttc ttggcgtctc gccggccaga cccctccctc      360
aaaggcgggg cctggagatc cacagctgga aagggcggag ccccagcagg gcagctggaa    420
aggggcgggg cctgacgcgc gcggctcgcc gcggcgggct gggggcgccc tggtctgcca    480
taaagtgaat gggcgccggc tggggtggc agtacgcggt gaggctcact ccctccgaga     540
gtccaggagc gcccgagcgg agaggcggcc cgggagcagg gggcggcccc cactccggc     600 cgggtgcccg gcccctggcc cctgcctgcc ctctagatcg ccgccgcagc cgccgctact    660
gggagtct                                                             668
```

PITX3 EXPRESSION PROMOTERS

FIELD OF THE INVENTION

The invention relates to gene promoters and regulatory elements. More specifically, the invention relates to novel PITX3 promoter compositions and related methods.

BACKGROUND

The PITX3 gene encodes a homeobox transcription factor, which is a member of the PITX subfamily of paired-like homeobox proteins. In the mammalian brain, PITX3 is expressed in midbrain dopaminergic neurons and is involved in molecular development of dopaminergic neurons in the substantia nigra and for postnatal survival of a subset of dopaminergic neurons in the ventral tegmental area (Smidt et al. 2004; Korotkova et al. 2005; Castillo-Carranza et al. 2008). A double mutation in the mouse PITX3 gene leads to abnormal lens and ocular development in aphakia mice (Rieger et al. 2001). The midbrain/dopaminergic neurons are absent in ak/ak mouse embryos, starting at day 12.5. Midbrain dopaminergic pathways are implicated in control of many brain functions, including those involved in psychiatric and neurological disorders, including Parkinson's disease (PD).

Castillo-Carranza et al. (2008) disclose a 4.8 kb mouse PITX3 promoter construct and analysis of its expression in a human neuroblastoma cell line.

Coulon et al. (2007) disclose a number of mouse PITX3 promoter construct and analysis of expression from these promoters in mouse embryonic development, particularly muscle-specific expression.

There exists a significant need for promoter elements which are capable of driving expression in specific cell types and/or in specific regions of the brain. Identification of minimal elements required for adequate expression and specificity will allow ease of use in expression constructs.

SUMMARY OF THE INVENTION

The present invention provides novel nucleic acid sequence compositions and methods relating to PITX3 promoters having a sequence other than a native PITX3 promoter.

In one embodiment of the invention, there is provided an isolated nucleic acid fragment comprising a PITX3 mini-promoter, wherein the PITX3 mini-promoter comprises a PITX3 regulatory element operably linked in a non-native conformation to a PITX3 basal promoter. The PITX3 promoter may have a nucleic acid sequence which is substantially similar in sequence and function to SEQ ID NO: 1. The PITX3 regulatory element may have a nucleic acid sequence which is substantially similar in sequence and function to SEQ ID NO: 2. The PITX3 basal promoter may have a nucleic acid sequence which is substantially similar in sequence and function to SEQ ID NO: 3. The PITX3 promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

In one embodiment, there is provided an expression vector comprising a PITX3 mini-promoter element, wherein the PITX3 mini-promoter element comprises a PITX3 regulatory element operably linked in a non-native conformation to a PITX3 basal promoter element. The PITX3 promoter may have a nucleic acid sequence which is substantially similar in sequence and function to SEQ ID NO: 1. The PITX3 regulatory element may have a nucleic acid sequence which is substantially similar in sequence and function to SEQ ID NO: 2. The PITX3 basal promoter may have a nucleic acid sequence which is substantially similar in sequence and function to SEQ ID NO: 3. The PITX3 promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT.

In one embodiment, there is provided a method for expressing a gene, protein, RNA interference molecule or the like in a cell, the method comprising introducing into the cell a expression vector comprising a PITX3 mini-promoter element, wherein the PITX3 mini-promoter element comprises a PITX3 regulatory element operably linked in a non-native conformation to a PITX3 basal promoter element. Cells of interest include, without limitation, cells of the peripheral or central nervous system and progenitors thereof, e.g. embryonic stem cells, neural stem cells, neurons, glial cells, astrocytes, microgial cells, etc. Cells of interest may also include cells of the eye, for instance retinal cells. The PITX3 promoter may have a nucleic acid sequence which is substantially similar in sequence and function to SEQ ID NO: 1. The PITX3 regulatory element may have a nucleic acid sequence which is substantially similar in sequence and function to SEQ ID NO: 2. The PITX3 basal promoter may have a nucleic acid sequence which is substantially similar in sequence and function to SEQ ID NO: 3. The PITX3 promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell a expression vector comprising a PITX3 mini-promoter element operably linked to an expressible sequence, wherein the PITX3 mini-promoter element comprises a PITX3 regulatory element operably linked in a non-native conformation to a PITX3 basal promoter element, and wherein the expressible sequence comprises a reporter gene. The PITX3 promoter element may have a nucleic acid sequence substantially similar in sequence and function to SEQ ID NO: 1. The PITX3 regulatory element may have a nucleic acid sequence substantially similar in sequence and function to SEQ ID NO: 2. The PITX3 basal promoter element may have a nucleic acid sequence substantially similar in sequence and function to SEQ ID NO: 3. In some embodiments, the cell is a peripheral or central nervous system cell or progenitors thereof, including, without limitation, embryonic stem cells, neural stem cells, glial cells, astrocytes, neurons and the like. In some embodiments, the cell is a cell of the eye, for instance a retinal cell. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In one embodiment of the invention, there is provided a method for monitoring or tracking the development or maturation of a cell, the method comprising: 1) introducing into the cell a expression vector comprising a PITX3 mini-promoter element operably linked to an expressible sequence, wherein the PITX3 mini-promoter element comprises a PITX3 regulatory element operably linked in a non-native conformation to a PITX3 basal promoter element, and wherein the expressible sequence comprises a reporter gene; and 2) detecting the expression of the reporter gene in the cell of in progeny of the cell as a means of determining the lineage, identity or developmental state of the cell or cell progeny. The PITX3 promoter element may have a nucleic acid sequence substantially similar in sequence and function to SEQ ID NO: 1. The PITX3 regulatory element may have a nucleic acid sequence substantially similar in sequence and function to SEQ ID NO: 2. The PITX3 basal promoter element may have a nucleic acid sequence substantially similar in sequence and function to SEQ ID NO: 3. In some embodiments, the cell is a peripheral or central nervous system cell or progenitors thereof, including, without limitation, embryonic stem cells, neural stem cells, glial cells, neurons and the like. In some embodiments, the cell is a cell of the eye, for instance a retinal cell.

SHORT DESCRIPTION OF FIGURES

FIG. 1—DNA expression vector (pEMS1302) into which PITX3 promoter elements were inserted for expression studies. The PITX3 promoter with a nucleic acid sequence corresponding to SEQ ID NO: 1 was inserted into the multiple cloning site (MCS) of the pEMS1302 vector such that it became operably linked to the enhanced green fluorescent protein (EGFP) reporter gene. The final construct, called PITX3-D, also contained the HPRT genomic targeting sequence, an ampicillin resistance gene (AmpR) for screening, and a transcriptional termination sequence (SV40 polyA), as well as other elements necessary for vector replication and gene expression.

Figure 2:
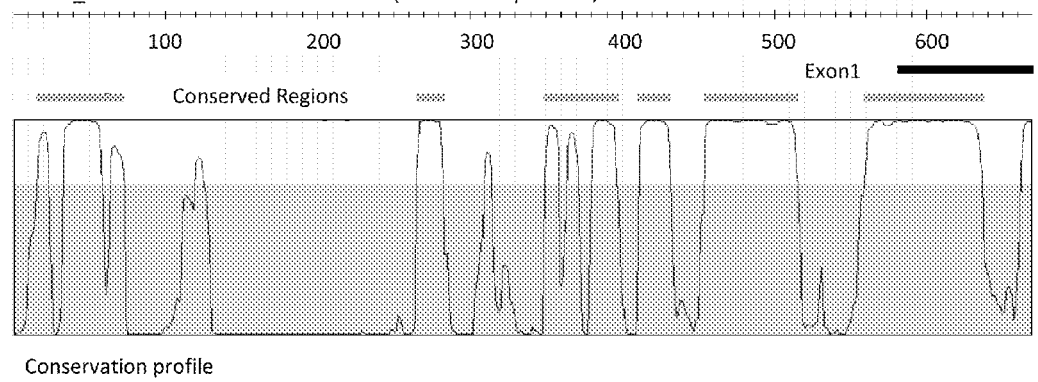
Figure 2:
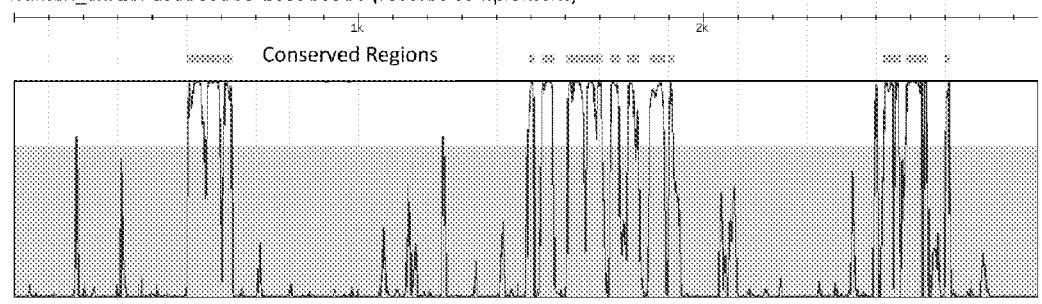

FIG. 2—PITX3 putative invariant regions for the basal promoter (A) and regulatory element (B). Each picture shows, from top to bottom, the human sequence, the non-coding conserved regions as blue boxes, the conservation profile between 28 species represented as PhastCons scores, ranging from 0 to 1, extracted from the UCSC genome browser, with the grey area delineating the 0.7 threshold used. In addition in A, the picture displays the exon overlapping the Prom region as a black box FIG. 3—Positive expression from the Ple162 MiniPromoter is detected in a small subpopulation of neurons in the vicinity of the ventral tegmental area (VTA), however, EGFP expression is not detected in this or any other brain region in germline mice. FIGS. A and A' illustrate the positive βGal staining from a typical germline mouse showing blue cells in the midbrain region bordering the fasciculus retroflexus. All positive germline mice show this same population of cell labelling. Double labelling for βgal and tyrosine hydroxylase (which identifies dopaminergic cell bodies and processes; FIGS. B and B') shows that the βgal-positive cells are not dopaminergic cells, but do border the dorsal edge of the main dopaminergic population of the VTA.

Figure 4:
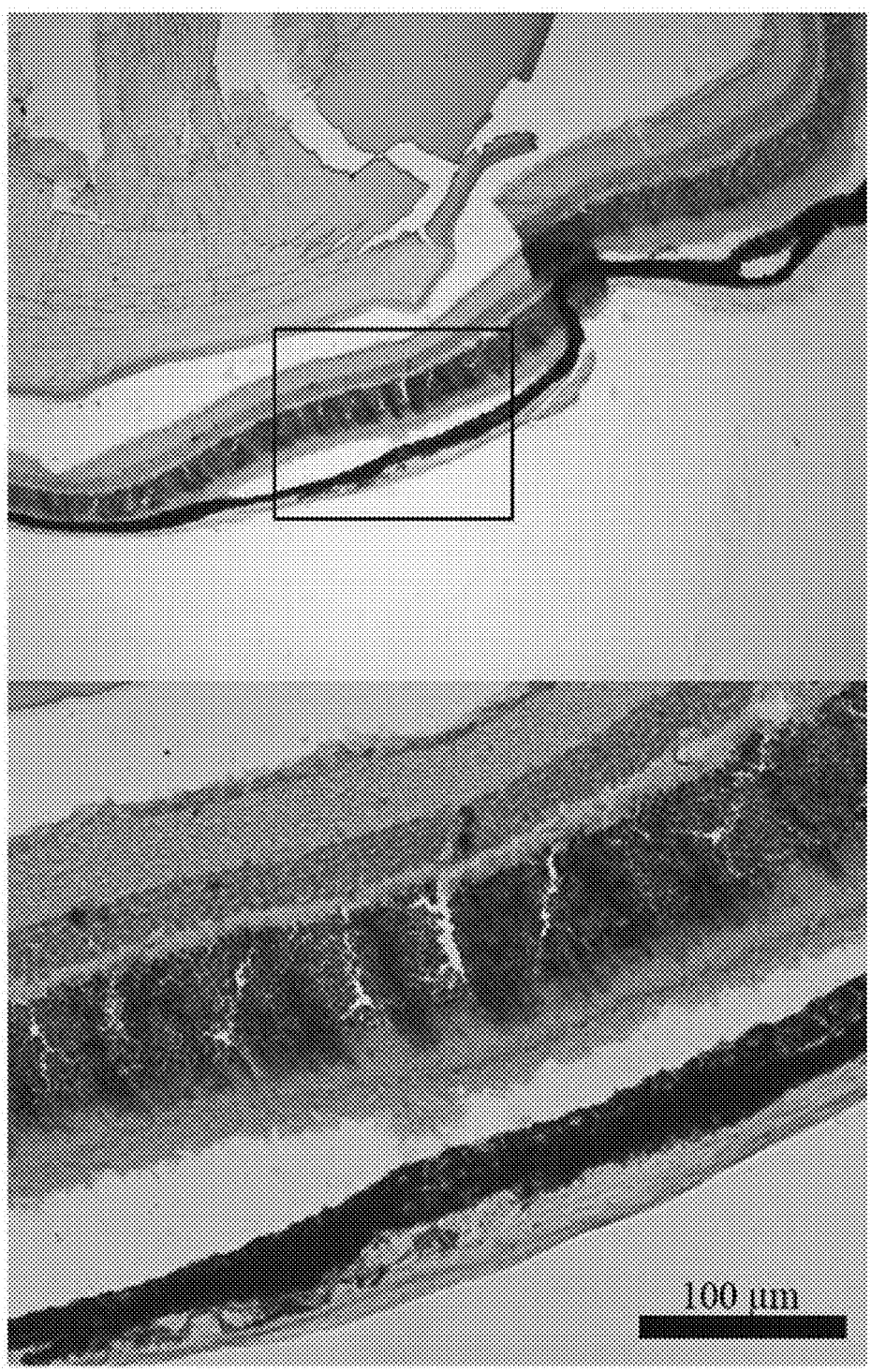

FIG. 4—Brightfield images of an adult germline mouse with Ple162 (PITX3) MiniPromoter driving EGFP/cre expression in a mouse carrying Gt(ROSA)26Sortm1Sor. Blue staining is β-galactosidase activity.

DETAILED DESCRIPTION

The compositions of the present invention include novel polynucleotides comprising PITX3 promoter elements (also referred to herein as PITX3 mini-promoters) as well as novel expression vectors comprising said PITX3 promoter elements (or mini-promoters). The present invention also includes various methods utilizing these novel PITX3 promoter (or mini-promoter) elements or expression vectors.

The term 'PITX3' refers to the gene which encodes the PITX3 protein, also referred to as PTX3 or CTPP4. The protein encoded by the PITX3 gene is a member of the PITX (or PTX) subfamily of paired-like homeodomain proteins. The human homolog of PITX3 is encoded by the human gene identified as EntrezGene #5309 and is located at chromosomal location 10q25. The protein encoded by human PITX3 has the Protein Accession #O75364.1 (Swiss-Prot). Other mammalian PITX3 homologs include but are not limited to: *Rattus norvegicus* (EntrezGene #29609, Protein Accession #P81062.2), *Mus musculus* (EntrezGene #18742, Protein Accession #O35160.1).

The term 'promoter' refers to the regulatory DNA region which controls transcription or expression of a gene and which can be located adjacent to or overlapping a nucleotide or region of nucleotides at which RNA transcription is initiated. A promoter contains specific DNA sequences which bind protein factors, often referred to as transcription factors, which facilitate binding of RNA polymerase to the DNA leading to gene transcription. A 'basal promoter', also referred to as a 'core promoter', usually means a promoter which contains all the basic necessary elements to promote transcriptional expression of an operably linked polynucleotide. Eukaryotic basal promoters typically, though not necessarily, contain a TATA-box and/or a CAAT box. A 'PITX3 basal promoter', in the context of the present invention and as used herein, is a nucleic acid compound having a sequence with at least 65%, at least 70%, at least 80%, at least 85%, at least 90%, at least 95%, or at least 99% similarity to SEQ ID NO: 3, and which comprises at least 4, usually at least 5, and may comprise all 6 of the identified conserved sequences listed in Table 1.

TABLE 1

List of conserved sequences in the human
PITX3 basal promoter - SEQ ID NO: 3.

| Start (relative to SEQ ID NO: 3) | End (relative to SEQ ID NO: 3) | Invariant sequence type |
|---|---|---|
| 116 | 172 | Conserved sequence |
| 365 | 382 | Conserved sequence |
| 449 | 496 | Conserved sequence |
| 511 | 531 | Conserved sequence |

TABLE 1-continued

List of conserved sequences in the human
PITX3 basal promoter - SEQ ID NO: 3.

| Start (relative to SEQ ID NO: 3) | End (relative to SEQ ID NO: 3) | Invariant sequence type |
|---|---|---|
| 554 | 614 | Conserved sequence |
| 659 | 736 | Conserved sequence |

The start and end coordinates of the sequences are relative to the full SEQ ID NO: 3 sequence. Conservation determined by alignment of 28 vertebrate species available through the UCSC genome browser.

A promoter may also include 'regulatory elements' that influence the expression or transcription by the promoter. Such regulatory elements encode specific DNA sequences which bind other factors, which may include but are not limited to enhancers, silencers, insulators, and/or boundary elements. A 'PITX3 regulatory element', in the context of the present invention and as used herein, is a nucleic acid compound having a sequence with at least 65%, at least 70%, at least 80%, at least 85%, at least 90%, at least 95%, or at least 99% similarity to SEQ ID NO: 2, and which comprises at least 8, usually at least 10, and may comprise all 12 of the identified conserved sequences listed in Table 2. The present invention provides, in certain embodiments as described herein, different promoters of the PITX3 gene. In some embodiments, the PITX3 promoter comprises a PITX3 regulatory element operably linked to a PITX3 basal promoter.

TABLE 2

List of conserved sequences in the human
PITX3 regulatory element - SEQ ID NO: 2.

| Start (relative to SEQ ID NO: 2) | End (relative to SEQ ID NO: 2) | Invariant sequence type |
|---|---|---|
| 504 | 597 | Conserved sequence |
| 608 | 632 | Conserved sequence |
| 1492 | 1507 | Conserved sequence |
| 1529 | 1563 | Conserved sequence |
| 1609 | 1707 | Conserved sequence |
| 1733 | 1759 | Conserved sequence |
| 1782 | 1815 | Conserved sequence |
| 1845 | 1889 | Conserved sequence |
| 2002 | 1913 | Conserved sequence |
| 2525 | 2571 | Conserved sequence |
| 2589 | 2652 | Conserved sequence |
| 2704 | 2715 | Conserved sequence |

The start and end coordinates of the sequences are relative to the full SEQ ID NO: 2 sequence.

The term 'operably linked', in the context of the present invention, means joined in such a fashion as to work together to allow transcription. In some embodiments of the invention, two polynucleotide sequences may be operably linked by being directly linked via a nucleotide bond. In this fashion, the two operably linked elements contain no intervening sequences and in being joined are able to direct transcription of an expression sequence. In other embodiments of the invention, two elements may be operably linked by an intervening compound, for instance a polynucleotide sequence of variable length. In such a fashion, the operably linked elements, although not directly juxtaposed, are still able to direct transcription of an expression sequence. Thus, according to some embodiments of the invention, one or more promoter elements may be operably linked to each other, and additionally be operably linked to a downstream expression sequence, such that the linked promoter elements are able to direct expression of the downstream expression sequence.

The term 'mini-promoter' refers to a promoter in which certain promoter elements are combined in a non-native conformation, usually in such a fashion as to reduce the overall size of the promoter compared to the native conformation. For example, after identification of critical promoter elements, using one or more of various techniques, the native sequences that intervene between identified elements may be partially or completely removed. Other non-native sequences may optionally be inserted between the identified promoter elements. A mini-promoter may provide certain advantages over native promoter conformations. For example, the smaller size of the mini-promoter may allow easier genetic manipulation, for example in the design and/or construction of expression vectors or other recombinant DNA constructs. In addition, the smaller size may allow easier insertion of DNA constructs into host cells and/or genomes, for example via transfection, transformation, etc. Other advantages of mini-promoters are apparent to one of skill in the art. In some embodiments of the invention, there are thus provided novel PITX3 mini-promoters comprising a PITX3 regulatory element operably linked in a non-native conformation to a PITX3 basal promoter. In general the spacing between the PITX3 regulatory element and the PITX3 basal promoter is not more than about 15 KB, generally not more than about 10 KB, usually not more than about 1 KB, more often not more than about 500 nt, and may be not more than about 100 nt, down to a direct joining of the two sequences.

The term 'expressible sequence' refers to a polynucleotide composition which is operably linked to a promoter element such that the promoter element is able to cause transcriptional expression of the expression sequence. An expressible sequence is typically linked downstream, on the 3'-end of the promoter element(s) in order to achieve transcriptional expression. The result of this transcriptional expression is the production of an RNA macromolecule. The expressed RNA molecule may encode a protein and may thus be subsequently translated by the appropriate cellular machinery to produce a polypeptide protein molecule. In some embodiments of the invention, the expression sequence may encode a reporter protein. Alternately, the RNA molecule may be an antisense, RNAi or other non-coding RNA molecule, which may be capable of modulating the expression of specific genes in a cell, as is known in the art.

The term 'RNA' as used in the present invention includes full-length RNA molecules, which may be coding or non-coding sequences, fragments, and derivatives thereof. For example, a full-length RNA may initially encompass up to about 20 Kb or more of sequence, and frequently will be processed by splicing to generate a small mature RNA. Fragments, RNAi, miRNA and anti-sense molecules may be smaller, usually at least about 18 nt. in length, at least about 20 nt in length, at least about 25 nt. in length, and may be up to about 50 nt. in length, up to about 100 nt in length, or more. RNA may be single stranded, double stranded, synthetic, isolated, partially isolated, essentially pure or recombinant. RNA compounds may be naturally occurring, or they may be altered such that they differ from naturally occurring RNA compounds. Alterations may include addition, deletion, substitution or modification of existing nucleotides. Such nucleotides may be either naturally occurring, or non-naturally occurring nucleotides. Alterations may also involve addition or insertion of non-nucleotide material, for instance at the end or ends of an existing RNA compound, or at a site that is internal to the RNA (ie. between two or more nucleotides).

The term 'nucleic acid' as used herein includes any nucleic acid, and may be a deoxyribonucleotide or ribonucleotide polymer in either single or double-stranded form. A 'polynucleotide' or 'nucleotide polymer' as used herein may include synthetic or mixed polymers of nucleic acids, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

A 'purine' is a heterocyclic organic compound containing fused pyrimidine and imidazole rings, and acts as the parent compound for purine bases, adenine (A) and guanine (G). 'Nucleotides' are generally a purine (R) or pyrimidine (Y) base covalently linked to a pentose, usually ribose or deoxyribose, where the sugar carries one or more phosphate groups. Nucleic acids are generally a polymer of nucleotides joined by 3' 5' phosphodiester linkages. As used herein 'purine' is used to refer to the purine bases, A and G, and more broadly to include the nucleotide monomers, deoxyadenosine-5'-phosphate and deoxyguanosine-5'-phosphate, as components of a polynucleotide chain. A 'pyrimidine' is a single-ringed, organic base that forms nucleotide bases, such as cytosine (C), thymine (T) and uracil (U). As used herein 'pyrimidine' is used to refer to the pyrimidine bases, C, T and U, and more broadly to include the pyrimidine nucleotide monomers that along with purine nucleotides are the components of a polynucleotide chain.

It is within the capability of one of skill in the art to modify the sequence of a promoter nucleic acid sequence, e.g. the provided basal promoter and regulatory sequences, in a manner that does not substantially change the activity of the promoter element, i.e. the transcription rate of an expressible sequence operably linked to a modified promoter sequence is at least about 65% the transcription rate of the original promoter, at least about 75% the transcription rate of the original promoter sequence, at least about 80%, at least about 90%, at least about 95%, at least about 99%, or more. Such modified sequences would be considered to be 'functionally similar' or to have 'functional similarity' or 'substantial functional similarity' to the unmodified sequence. Such modifications may include insertions, deletions which may be truncation of the sequence or internal deletions, or substitutions. The level of sequence modification to an original sequence will determine the 'sequence similarity' of the original and modified sequences. Modification of the promoter elements of the present invention in a fashion that does not significantly alter transcriptional activity, as described above would result in sequences with 'substantial sequence similarity' to the original sequence i.e. the modified sequence has a nucleic acid composition that is at least about 65% similar to the original promoter sequence, at least about 75% similar to the original promoter sequence, at least about 80%, at least about 90%, at least about 95%, at least about 99%, or more similar to the original promoter sequence. Thus, mini-promoter elements which have substantial functional and/or sequence similarity are herein described and are within the scope of the invention.

An 'RNA interference molecule', or 'RNA interference sequence' as defined herein, may include, but is not limited to, an antisense RNA molecule, a microRNA molecule or a short hairpin RNA (shRNA) molecule. Typically, RNA interference molecules are capable of target-specific modulation of gene expression and exert their effect either by mediating degradation of the mRNA products of the target gene, or by preventing protein translation from the mRNA of the target gene. The overall effect of interference with mRNA function is modulation of expression of the product of a target gene. This modulation can be measured in ways which are routine in the art, for example by Northern blot assay or reverse transcriptase PCR of mRNA expression, Western blot or ELISA assay of protein expression, immunoprecipitation assay of protein expression, etc.

An 'antisense RNA molecule', as used herein, is typically a single stranded RNA compound which binds to complementary RNA compounds, such as target mRNA molecules, and blocks translation from the complementary RNA compounds by sterically interfering with the normal translational machinery. Specific targeting of antisense RNA compounds to inhibit the expression of a desired gene may design the antisense RNA compound to have a homologous, complementary sequence to the desired gene. Perfect homology is not necessary for inhibition of expression. Design of gene specific antisense RNA compounds, including nucleotide sequence selection and additionally appropriate alterations, are known to one of skill in the art.

The term 'microRNA molecule', 'microRNA' or 'miRNA', as used herein, refers to single-stranded RNA molecules, typically of about 21-23 nucleotides in length, which are capable of modulating gene expression. Mature miRNA molecules are partially complementary to one or more messenger RNA (mRNA) molecules, and their main function is to down-regulate gene expression. Without being bound by theory, miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end. The remaining strand, known as the anti-guide or passenger strand, is degraded as a RISC complex substrate. After integration into the active RISC complex, miRNAs base pair with their complementary mRNA molecules and induce mRNA degradation by argonaute proteins, the catalytically active members of the RISC complex. Animal miRNAs are usually complementary to a site in the 3' UTR whereas plant miRNAs are usually complementary to coding regions of mRNAs.

The term 'short hairpin RNA' or 'shRNA' refers to RNA molecules having an RNA sequence that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA Polymerase III whereas miRNA is transcribed by RNA Polymerase II. Techniques for designing target specific shRNA molecules are known in the art.

An 'expression vector' is typically a nucleic acid molecule which may be integrating or autonomous, (i.e. self-replicating), and which contains the necessary components to achieve transcription of an expressible sequence in a target cell, when introduced into the target cell. Expression vectors may include plasmids, cosmids, phage, YAC, BAC, minichromosomes, viruses, e.g. retroviruses, adenovirus, lentivirus, SV-40, and the like; etc. Many such vectors have been described in the art and are suitable for use with the promoters of the present invention. Expression vectors of the present invention include a promoter as described herein, operably linked to an expressible sequence, which may also be optionally operably linked to a transcription termination sequence, such as a polyadenylation sequence. The expression vector optionally contains nucleic acid elements which confer host selectivity, elements that facilitate replication of the vector, elements that facilitate integration of the vector into the genome of the target cell, elements which confer properties, for example antibiotic resistance, to the target cell which allow selection or screening of transformed cells and the like. Techniques and methods for design and construction of expression vectors are well known in the art.

It may be desirable, when driving expression of an expressible sequence with a particular promoter system to have the expression occur in a stable and consistent manner. A factor that has been shown to affect expression is the site of integration of an expression vector or construct into the genome of the target cell, sometimes called 'position effects'. Such position effects may be caused by, for example, local chromatin structure which affects expression of sequences from that region of the genome. One method to control for position effects when integrating an expression vector or construct into the genome of a target cell is to include a 'genomic targeting sequence' in the vector or construct that directs integration of the vector or construct to a specific genomic site. As an example, the hypoxanthine phosphoribosyltransferase (HPRT) gene has been used successfully for this purpose (Bronson et al. 1996; Jasin et al. 1996). The HPRT gene has additional advantages as a genomic targeting sequence, for instance its concomitant use as a selectable marker system. Other genomic targeting sequences that may be useful in the present invention are described in the art, for instance (Jasin et al. 1996; van der Weyden et al. 2002). The genomic targeting signals as described herein are useful in certain embodiments of the present invention.

Introduction of nucleic acids or expression vectors may be accomplished using techniques well known in the art, for example microinjection, electroporation, particle bombardment, or chemical transformation, such as calcium-mediated transformation, as described for example in Maniatis et al. 1982, Molecular Cloning, A laboratory Manual, Cold Spring Harbor Laboratory or in Ausubel et al. 1994, Current protocols in molecular biology, Jolm Wiley and Sons.

PITX3 Promoters

The present invention herein provides novel PITX3 mini-promoter sequences which are capable of effecting transcriptional expression in a spatial and temporal fashion in the brain. The PITX3 mini-promoters of the invention comprise PITX3 promoter elements joined in a non-native configuration, thus providing advantageous characteristics. Also provided are novel expression vector compositions comprising PITX3 mini-promoters which allow consistent specific spatiotemporal transcription of expression sequences. Also provided are novel methods utilizing these PITX3 mini-promoters and expression vectors.

The PITX3 promoters of the invention, as described herein, are referred to as 'mini-promoters' to reflect fact that the mini-promoters comprise PITX3 promoter elements that are joined by non-native sequences. In this context, the native intervening sequences may have been partially or completely removed, and optionally may have been replaced with non-native sequences. In such a fashion, the natural spacing of the promoter elements, for instance the human PITX3 regulatory element corresponding to SEQ ID NO: 2 and the human PITX3 basal promoter element corresponding to SEQ ID NO: 3, or sequences with substantial functional and/or sequence equivalence, is altered. An advantage of such non-native mini-promoters is that the removal of native intervening sequences reduces the size of the mini-promoter while maintaining the functional activity of the promoter, thus improving the utility of the mini-promoter for various applications.

The inventors have demonstrated, as illustrated in the non-limiting Working Examples, that a human PITX3 mini-promoter having a sequence corresponding to SEQ ID NO: 1, and which is comprised of a human PITX3 regulatory element having a nucleic acid sequence corresponding to SEQ ID NO: 2 operably linked in a non-native conformation to a human PITX3 basal promoter having a nucleic acid sequence corresponding to SEQ ID NO: 3, is capable of directing expression of an expressible sequence which is operably linked downstream of the PITX3 promoter in specific cell types in different regions of the brain. The PITX3 regulatory element (SEQ ID NO: 2) and PITX3 basal promoter element (SEQ ID NO: 3) have sequences which are identical to those found upstream of the human PITX3 gene, found on chromosome 10 of the human genome. It is within the skill of one in the art to locate and determine these relative positions based on published sequence information for this gene, for instance found in the GenBank or PubMed public databases. It is understood that these genomic coordinates and relative positions are provided for the purposes of context, and that if any discrepancies exist between published sequences and the sequence listings provided herein, then the sequence listings shall prevail.

Promoters of the present invention may be modified with respect to the native regulatory and/or native basal promoter sequence. In general, such modifications will not change the functional activity of the promoter with respect to cell-type selectivity; and to the rate of transcription in cells where the promoter is active. The modified promoter provide for a transcription rate of an expressible sequence operably linked to a modified promoter sequence that is at least about 75% the transcription rate of the promoter sequence of SEQ ID NO:1, at least about 80%, at least about 90%, at least about 95%, at least about 99%, or more. Methods of assessing promoter strength and selectivity are known in the art, including, for example, expression of a reporter sequence in a cell in vivo or in vitro, and quantitating the reporter activity.

Modifications of interest include deletion of terminal or internal regions, and substitution or insertion of residues. Applicants have identified 18 conserved sequences in the PITX3 promoter (Table 1), where 12 such conserved sequences are present in the regulatory element, and 6 conserved sequences are present in the basal promoter. A promoter of interest in the present invention comprises at least 10, usually at least 15, and may comprise all 18 of the identified conserved sequences. The spacing of conserved sequences may be the same as the native spacing, or it may be different than the native spacing. The order of the conserved sequences may be the same as the native order or the sequences may be rearranged. Sequences set forth in SEQ ID NO:1 that are not conserved may be deleted or substituted, usually modifications that retain the spacing between conserved sequences is preferred. In general the spacing between the regulatory element and the basal promoter is not more than about 10 KB, generally not more than about 1 KB, usually not more than about 500 nt, and may be not more than about 100 nt, down to a direct joining of the two sequences.

TABLE 3

List of conserved sequences in SEQ ID NO: 1.

| Start (relative to SEQ ID NO: 1) | End (relative to SEQ ID NO: 1) | Invariant sequence type |
|---|---|---|
| 504 | 597 | Conserved sequence |
| 608 | 632 | Conserved sequence |
| 1492 | 1507 | Conserved sequence |
| 1529 | 1563 | Conserved sequence |
| 1609 | 1707 | Conserved sequence |
| 1733 | 1759 | Conserved sequence |
| 1782 | 1815 | Conserved sequence |
| 1845 | 1889 | Conserved sequence |
| 2002 | 1913 | Conserved sequence |
| 2525 | 2570 | Conserved sequence |
| 2589 | 2652 | Conserved sequence |
| 2704 | 2715 | Conserved sequence |
| 2987 | 3043 | Conserved sequence |
| 3236 | 3253 | Conserved sequence |
| 3320 | 3367 | Conserved sequence |
| 3382 | 3402 | Conserved sequence |
| 3425 | 3485 | Conserved sequence |
| 3530 | 3607 | Conserved sequence |

The start and end coordinates of the sequences are relative to the full SEQ ID NO: 1 sequence.

In some embodiments of the invention, there is thus provided an isolated nucleic acid fragment comprising a PITX3 mini-promoter, wherein the PITX3 promoter comprises a PITX3 regulatory element operably linked in a non-native conformation to a PITX3 basal promoter. In certain embodiments of the invention, the PITX3 promoter may have a nucleic acid sequence which is substantially similar in sequence and function to SEQ ID NO: 1. In some embodiments, the PITX3 regulatory element may have a nucleic acid sequence which is substantially similar in sequence and function to SEQ ID NO: 2. In some embodiments, the PITX3 basal promoter may have a nucleic acid sequence which is substantially similar in sequence and function to SEQ ID NO: 3. The PITX3 promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like.

It is an object of the present invention to provide means of expressing a gene, protein, RNA interference molecule or the like in a cell, tissue or organ. As such, the inventors thus provide novel expression vectors comprising PITX3 mini-promoters which are capable of accomplishing this task. In some embodiments of the invention, there is provided an expression vector comprising a PITX3 promoter element, wherein the PITX3 promoter element comprises a PITX3 regulatory element operably linked in a non-native conformation to a PITX3 basal promoter element. The PITX3 promoter element may have a nucleic acid sequence substantially similar in sequence and function to SEQ ID NO: 1. The PITX3 regulatory element may have a nucleic acid sequence substantially similar in sequence and function to SEQ ID NO: 2. The PITX3 basal promoter element may have a nucleic acid sequence substantially similar in sequence and function to SEQ ID NO: 3. The PITX3 promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expression vector may further comprise a genomic targeting sequence. The genomic targeting sequence may be HPRT, e.g. human HPRT, mouse HPRT, etc.

The inventors have herein demonstrated that expression vectors comprising novel PITX3 mini-promoter elements are capable of directing transcription of an expression sequence in specific cell types in specific regions of the brain, most notably neuronal cells in the midbrain region of the brain. In some embodiments of the invention, there is thus provided a method for expressing a gene, protein, RNA interference molecule or the like in the targeted cells of the brain or the eye. Cells of interest include, without limitation, cells of the peripheral or central nervous system and progenitors thereof, e.g. embryonic stem cells, neural stem cells, neurons, glial cells, astrocytes, microglial cells, etc., and cells of the eye, e.g. retinal cells. The method comprises introducing into a cell or progenitor cell thereof an expression vector comprising a PITX3 mini-promoter element, wherein the PITX3 mini-promoter element comprises a PITX3 regulatory element operably linked in a non-native conformation to a PITX3 basal promoter element. The PITX3 promoter element may have a nucleic acid sequence substantially similar in sequence and function to SEQ ID NO: 1. The PITX3 regulatory element may have a nucleic acid sequence substantially similar in sequence and function to SEQ ID NO: 2. The PITX3 basal promoter element may have a nucleic acid sequence substantially similar in sequence and function to SEQ ID NO: 3. The PITX3 promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expression vector may thus further comprise a genomic targeting sequence. The genomic targeting sequence may be HPRT.

In other embodiments of the invention, there is provided a method for identifying or labeling a cell, the method comprising introducing into the cell a expression vector comprising a PITX3 mini-promoter element operably linked to an expressible sequence, wherein the PITX3 mini-promoter element comprises a PITX3 regulatory element operably linked in a non-native conformation to a PITX3 basal promoter element, and wherein the expressible sequence comprises a reporter gene. The PITX3 promoter element may have a nucleic acid sequence substantially similar in sequence and function to SEQ ID NO: 1. The PITX3 regulatory element may have a nucleic acid sequence substantially similar in sequence and function to SEQ ID NO: 2. The PITX3 basal promoter element may have a nucleic acid sequence substantially similar in sequence and function to SEQ ID NO: 3. The inventors have demonstrated that expression vectors comprising certain human PITX3 promoter elements are capable of expression in specific regions of the brain, most notably neuronal cells in the midbrain region of the brain. In some embodiments, the cell is a peripheral or central nervous system cell or progenitors thereof, including, without limitation, embryonic stem cells, neural stem cells, glial cell, neuronal cells, astrocytes, and the like. The inventors have also demonstrated expression in retinal cells, thus in some embodiments, the cell is a cell of the eye, for instance a retinal cell. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In further embodiments of the invention, there is provided a method for monitoring or tracking the development or maturation of a neuron. The method comprises: 1) introducing into a progenitor to a neuronal cell, e.g. an embryonic stem cells, neural stem cell, neuronal progenitor cell, neuronal cell, etc., an expression vector comprising a PITX3 mini-promoter element operably linked to an expressible sequence, wherein the PITX3 mini-promoter element comprises a PITX3 regulatory element operably linked in a nonnative conformation to a PITX3 basal promoter element, and wherein the expressible sequence comprises a reporter gene; and 2) detecting the expression of the reporter gene in neuronal cell progeny of the progenitor cells as a means of determining the lineage, identity or developmental state of the progenitor cell or progeny thereof. In such a fashion, one may be able to follow the development of a parent cell as it differentiates into more mature cells. As an example, one could introduce a expression vector comprising the aforementioned PITX3 promoter elements into a pluripotent stem cell, monitor the expression of the reporter gene that is being expressed by the PITX3 promoter elements during the maturation and differentiation of the stem cell and thus determine the state of maturation, for instance in the differentiation of the pluripotent stem cell into a neuronal cell. The inventors have demonstrated that the PITX3 promoter elements described herein direct transcriptional expression in certain neuronal cell types, and so detection of reporter gene expression in a cell would thus be indicative of the cellular identity of the cell as being a neuronal cell. In other embodiments, rather than a neuronal cell, the method may utilize a retinal cell.

The inventors herein further describe the present invention by way of the following non-limiting examples:

WORKING EXAMPLES

General Methods

Expression vector. The nucleic acid fragment corresponding to SEQ ID NO: 1 was inserted into the multiple cloning site of the pEMS1302 (see FIG. 1) to produce the expression vector PITX3-D.

Derivation of mEMS1204 embryonic stem cells. Blastocysts were obtained from natural mating of B6-Hprt1$^{b-m3}$ females to 129-ROSA26 males at 3.5 dpc. Blastocysts were flushed from uterine horns as per (Hogan et al. 1994), cultured in EmbryoMax® KSOM with ½ Amino Acids, Glucose and Phenol Red (Cat #MR-121, Millipore/Chermicon, Temecula, Calif.) for 3-5 h, and then transferred onto mitomycin C (mitC; Cat#M4287, Sigma, Oakville, ON) mitotically inactivated B6-Hprt1$^{b-m3}$, B6129F1, or 129 mouse embryonic feeders (MEFs) derived from 13.5-day post-coital embryos (Ponchio et al. 2000) in 96-well plates containing KSR-ESC (Knockout™ D-MEM, Cat#10829-018, Invitrogen, Burlington, ON) with 2 mM L-glutamine (Cat#25030-081, Invitrogen, Burlington, ON), 0.1 mM MEM nonessential amino acid solution (Cat#11140-050, Invitrogen, Burlington, ON) and 16% Knockout™ Serum Replacement (Cat#10828-028, Invitrogen, Burlington, ON)) media (MEF media was replaced 3-5 hour prior to transfer). Blastocysts were cultured as per (Cheng et al. 2004) with the following modifications: Cells were cultured for 7-9 days in KSR-ESC with minimal disturbance (checked on day 2 to determine if the blastocysts had 'hatched' out of the zona pellucida) and no media changes. Blastocysts which hatched and had a well developed ICM (inner cell mass) were treated with 20 µl 0.25% trypsin-EDTA (Invitrogen, Burlington, ON) for 5 min at 37° C., triturated with a 200 µl pipetman, inactivated with 30 µl 0.5 mg/ml soybean trypsin inhibitor (Invitrogen, Burlington, ON), and brought up to 200 µl with KSR-ESC, then transferred individually to a 24-well MEF plate containing 1800 µl KSR-ESC, for a total volume of 2 ml. Beginning 4 days later, KSR-ESC media was replaced with FBS-ESC media (DMEM (Cat #11960-069, Invitrogen, Burlington, ON) with 2 mM L-glutamine (Invitrogen, Burlington, ON), 0.1 mM MEM nonessential amino acid solution (Invitrogen, Burlington, ON), 16% ES Cell Qualified fetal bovine serum (FBS, Invitrogen, Burlington, ON) and 0.01% β-mercaptoethanol (Sigma, Oakville, ON) in 25%, 50%, 75% proportions (respectively) to adapt the cells to FBS containing media. On day 7 the cells were trypsinized to one well of a 24 well plate containing 1 ml of 100% FBS-ESC media, with daily media replacement. Once confluent, wells containing ESC colonies were expanded 3×24 wells (with MEFs), then passaged to 3×24 (with MEFs) and 3×12 well (plastic—no MEFs) for DNA analysis. Once confluent, the 3×24 wells were combined, aliquoted (3 vials), and frozen in ESC-freeze media (50% FBS, 40% FBS-ESC media, 10% DMSO (Sigma, Oakville, ON), and the 3×12 well treated with lysis buffer (Fisher Scientific, Ottawa, ON), mixed and aliquoted. Cultures were genotyped for X & Y chromosomes (Clapcote and Roder 2005), Gt(ROSA)26Sor$^{tm1Sor}$ and WT alleles and Hprt1$^{b-m3}$ and WT alleles. B6129F1-Gt(ROSA)26Sor$^{tm1Sor}$/+, Hprt1$^{b-m3}$/Y and B6129F1-Gt(ROSA)26Sor$^{tm1Sor}$+/+, Hprt1$^{b-m3}$/Y cell lines were identified.

Knock-in at the Hprt1 locus The PITX3-D plasmid DNA was purified with Qiagen Maxi Kit (Qiagen, Mississauga, ON), resuspended in 10:1 Tris-EDTA (TE, pH7.0) buffer, and linearized with I-SceI (New England Biolabs, Pickering, ON). Linearized plasmid DNA was resuspended in 85 µl of TE (10:0.1) to a final concentration of 187.5 ng/µl. mEMS1204 ESCs were grown to confluence on 4-6 T75 flasks of mitC treated Hprt1$^{b-m3}$ mouse embryonic feeders (MEFs) in FBS-ESC media. ESCs (1.7-2.5×10$^7$) in 720 µl 1×PBS were added to the linearized DNA and electroporated in a 4 mm electroporation cuvette (Bio-Rad Genepulser, Mississauga, ON), at 240 V, 50 µF, 6-10 msec pulse, immediately resuspended in a total volume of 5 ml of FBS-ESC media and plated onto 5×100 mm dishes of mitC B6129F1 MEFs in a total volume of 12 ml/100 mm dish. 24-36 h post-electroporation, correctly targeted homologous recombinants were selected for using HAT media (FBS-ESC media containing 1×HAT ((0.1 mM sodium hypoxanthine, 0.4 mM aminopterin, 0.16 mM thymidine), Cat#21060-017, Invitrogen, Burlington, ON). HAT media was changed every day for the first 3 days, and then every 3$^{rd}$ day thereafter, for up to 10 days. Individual colonies were counted and, typically, no more than 2 isolated colonies were picked per 100 mm dish to optimize for independent homologous recombination events. These colonies were expanded under standard protocols for verification of the desired recombination event.

Derivation of knock-in mice. Chimeric mice from untargeted and targeted ESCs were generated by microinjection (Hogan et al. 1994) into B6 (E14TG2a derived) and B6-Alb (E14TG2a and mEMS1204 derived) E3.5 blastocysts, or co-culture(Lee et al. 2007) with diploid ICR (Charles River, Wilmington Wash. Stock#022) E2.5 morula (cultured overnight to the blastocyst stage), followed by implantation into the uterine horns of 2.5 day pseudopregnant ICR females. Chimeras were identified and coat color chimerism determined as outlined below.

Male chimeras derived from the E14TG2a cell lines were mated with B6 or B6-Alb females, and germline transmission was identified in the former case by the transmission of the dominant $A^w$ (nonagouti; white bellied agouti) allele, making the progeny appear brown with a cream belly, or in the later case by the combination of $A^w$ and $Tyr^{c-ch}$ (tyrosinase; chinchilla), making the progeny appear golden. Non-germline progeny from the cross to B6 were homozygous for the recessive a (nonagouti; nonagouti) allele and appeared black, whereas non-germline progeny from the cross to B6-Alb were homozygous for the recessive $Tyr^c$ (tyrosinase; albino) allele and appeared white.

Male chimeras derived from the mEMS1204 cell lines were mated with B6-Alb females, and germline transmission identified by the presence of the dominant $Tyr^+$ (tyrosinase; wild type) and the $A^w$ (nonagouti; white bellied agouti) or a (nonagouti; nonagouti) alleles making the progeny appear brown with a cream belly or black, respectively. Non-germline progeny were homozygous for the recessive $Tyr^{c-2J}$ (tyrosinase; albino 2 Jackson) allele and appear white. All germline female offspring should carry the knock-in X Chromosome and were mated with B6 males. N2 offspring were analyzed for the presence of the KI allele by PCR.

Determination of coat color chimerism. E14TG2a- and mEMS1204-derived chimeras were identified and level of coat color chimerism determined as follows. E14TG2a ESCs, homozygous for $A^w$ and $Tyc^{c-ch}$ as they are derived from the 129/OlaHsd strain (Hooper et al. 1987a; Hooper et al. 1987b), will produce chimeras with cream/chinchilla and agouti patches on a black background when injected into B6 blastocysts. The cream/chinchilla patches result from melanocytes derived solely from the ESCs ($A^w/A^w$, $Tyr^{c-ch}/Tyr^{c-ch}$), whereas agouti patches result from melanocytes that are a mixture of ESC ($A^w/A^w$, $Tyr^{c-ch}/Tyr^{c-ch}$) and host (a/a, $Tyr^+/Tyr^+$). However, E14TG2a ESCs, when injected into B6-Alb (a/a, $Tyr^c/Tyr^c$) produce chimeras with chinchilla and light chinchilla coat color patches on a white background. The former is derived solely from the ESCs ($A^w/A^w$, $Tyr^{c-ch}/Tyr^{c-ch}$), whereas the latter is again a mix of the ESC ($A^w/A^w$, $Tyr^{c-ch}/Tyr^{c-ch}$) and host (a/a, $Tyr^c/Tyr^c$). mEMS1204-derived chimeras were identified and coat color chimerism determined in the same manner. mEMS1204 ESCs, heterozygous $A^w$/a and homozygous for the wild type $Tyr^+$ alleles will produce chimeras with agouti and black patches on a white background when injected into B6-Alb blastocysts. The agouti patches result from melanocytes derived solely from the ESCs ($A^w$/a, $Tyr^+/Tyr^+$), whereas 'black' patches result from melanocytes that are a mixture of ESC ($A^w$/a, $Tyr^+/Tyr^+$) and host (a/a, $Tyr^{c-2J}/Tyr^{c-2J}$). For E14TG2a injections into B6 and mEMS1204 injections into B6-Alb, overall chimerism was calculated by summing the percent of coat color patches derived solely from the ESC, plus half the percent of the ESC+host areas, where we conservatively estimated that half the melanocytes derive from the ESC and half from the host. For E14TG2a injections into B6-Alb, the similarity between chinchilla and light chinchilla on a white background presented difficulty when attempting to estimate overall coat color chimerism. As such, we estimated the percent chimerism based solely on the total chimerism observed when compared to a white mouse, resulting in slightly inflated overall percent chimerism for this small cohort of mice.

Immunohistochemistry and Immunofluorescence. Adult male chimeric and age matched control mice were perfused with 4% paraformaldehyde (PFA) as previously described (Young et al. 2002). Whole brains were dissected out and post-perfusion immersion fixed with PFA for 2-3 hours at 4° C. Brains were then transferred to 20% sucrose at 4° C. overnight with gentle shaking. The brains were cryostat sectioned sagittally at 12-14 µm and mounted on superfost-plus slides (Cat#12-550-15, ThermoFisher Scientific, Waltham, Mass.). EGFP expression was detected by direct fluorescence of EGFP or by indirect immunofluorescence with anti-GFP antibodies (Abcam, Cambridge, Mass.) using a BioRad confocal laser scanning microscope (CLSM, BioRad, Hercules, Calif.). For double label immunofluorescence analyses to determine cell types in the cerebellum, anti-GFAP was used in conjunction with direct EGFP fluorescence and imaged by CLSM (Liu et al. 2007). In brief, slide mounted brain sections, were permeabilized with phosphate buffered saline containing 0.1% triton-X100 (PBST), blocked with PBST containing 5% normal horse serum and 1% BSA, then incubated with primary antibodies overnight at room temperature in a humid chamber. Following three washes with PBST, the tissue were incubated with secondary antibodies (goat anti-rabbit-Alexa-594 conjugate, Molecular Probes, Eugene, Oreg.). The slides were counterstained with TOTO3/DAPI (1 µM each) for labeling all nuclei in confocal images. Bright field analyses were also conducted following immunocytochemical detection of anti-GFP using the Vectastain ABC kit and DAB as the chromogen to give a brown reaction product following the manufacturer's directions. Bright field images were visualized on a Zeiss Axiovert microscope and Axiovision Software (Carl Zeiss Microimaging, Thornwood, N.Y.).

Example 1

Selection of PITX3D Promoter Elements

Under the assumption that sequences under selective pressure will be more conserved than those that are not, cross-species comparisons, or phylogenetic footprinting, were identified as a means to predict regulatory regions. The two mammalian species with the best evolutionary distance to use for this approach are human and mouse. In the specific case of PITX3, the conservation level between human and mouse was computed taking into consideration the non-coding sequence located between the upstream gene (GBF1) (where "upstream" refers to the neighbouring gene adjacent to the first exon of PITX3) and the final exon of PITX3, including all intron sequences. PITX3 being involved in development, the conservation is higher than average and a threshold of 75% identity was set up to select our candidate regulatory regions (FIG. 2). The PITX3 basal promoter (SEQ ID NO: 3) and regulatory region (SEQ ID NO: 2) were chosen based on these criteria.

Example 2

Expression of Reporter in Neuronal and Retinal Cells by PITX3-D Promoter Element The PITX3-D DNA expression vector comprising the PITX3 promoter element corresponding to SEQ ID NO: 1

Figure 3:
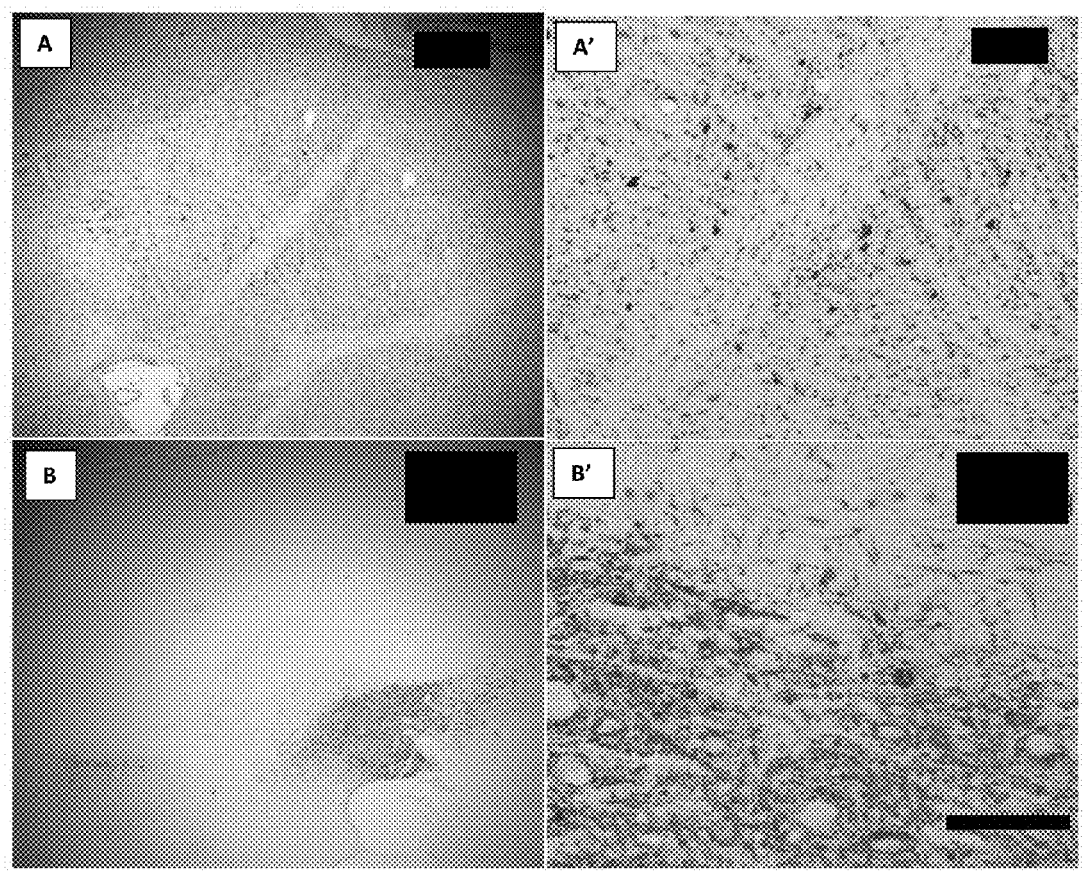

(which is itself comprised of SEQ ID NO: 2 linked to SEQ ID NO: 3) was introduced into mouse embryonic stem cells (ESCs) at the HPRT locus. The ESCs were used to generate genetically modified mice containing PITX3-D. Immunohistochemical and immunofluorescence analysis of mouse brain tissue slices revealed βGal reporter expression in a small subpopulation of neurons in the vicinity of the ventral tegmental area (VTA) of the brain (FIG. 3). Expression analysis also revealed expression in the retinal (FIG. 4).

REFERENCES

Bronson, S. K., E. G. Plaehn, et al. (1996). "Single-copy transgenic mice with chosen-site integration."*Proc Natl Acad Sci USA* 93(17): 9067-72.
Castillo-Carranza, D. L., H. Rodriguez-Rocha, et al. (2008). "Pitx3 promoter directs Cre-recombinase specifically in a human neuroblastoma cell line." *Mol Cell Biochem* 309(1-2): 223-7.
Cheng, J., A. Dutra, et al. (2004). "Improved generation of C57BL/6J mouse embryonic stem cells in a defined serum-free media." *Genesis* 39(2): 100-4.
Clapcote, S. J. and J. C. Roder (2005). "Simplex PCR assay for sex determination in mice." *Biotechniques* 38(5): 702, 704, 706.
Hogan, B., R. Beddington, et al. (1994). *Manipulating the mouse*. Cold Spring Harbor, Cold Spring Harbor Laboratory Press.
Hooper, M., K. Hardy, et al. (1987a). "HPRT-deficient (Lesch-Nyhan) mouse embryos derived from germline colonization by cultured cells." *Nature* 326(6110): 292-5.
Hooper, M., K. Hardy, et al. (1987b). "HPRT-deficient (Lesch-Nyhan) mouse embryos derived from germline colonization by cultured cells." *Nature* 326: 292-295.
Jasin, M., M. E. Moynahan, et al. (1996). "Targeted transgenesis." *Proc Natl Acad Sci USA* 93(17): 8804-8.
Korotkova, T. M., A. A. Ponomarenko, et al. (2005). "Differential expression of the homeo box gene Pitx3 in midbrain dopaminergic neurons." *Eur J Neurosci* 22(6): 1287-93.
Lee, K. H., C. K. Chuang, et al. (2007). "An alternative simple method for mass production of chimeric embryos by coculturing denuded embryos and embryonic stem cells in Eppendorf vials." *Theriogenology* 67(2): 228-37.
Liu, L., E. E. Geisert, et al. (2007). "A transgenic mouse class-III beta tubulin reporter using yellow fluorescent protein." *Genesis* 45(9): 560-9.
Ponchio, L., L. Duma, et al. (2000). "Mitomycin C as an alternative to irradiation to inhibit the feeder layer growth in long-term culture assays." *Cytotherapy* 2(4): 281-6.
Rieger, D. K., E. Reichenberger, et al. (2001). "A double-deletion mutation in the Pitx3 gene causes arrested lens development in aphakia mice." *Genomics* 72(1): 61-72.
Smidt, M. P., S. M. Smits, et al. (2004). "Homeobox gene Pitx3 and its role in the development of dopamine neurons of the substantia nigra." *Cell Tissue Res* 318(1): 35-43.
van der Weyden, L., D. J. Adams, et al. (2002). "Tools for targeted manipulation of the mouse genome."*Physiol Genomics* 11(3): 133-64.
Young, K. A., M. L. Berry, et al. (2002). "Fierce: a new mouse deletion of Nr2e1; violent behaviour and ocular abnormalities are background-dependent." *Behav Brain Res* 132(2): 145-58.

What is claimed is:

1. An isolated polynucleotide comprising a PITX3 regulatory element with at least 95% sequence identity to SEQ ID NO:2 operably joined to a PTIX3 basal promoter with at least 95% sequence identity to SEQ ID NO:3, wherein the spacing between the PITX3 regulatory element and the PITX3 basal promoter is not more than 500 nucleotides (nt).

2. The isolated polynucleotide of claim 1, operably linked to an expressible sequence.

3. A vector comprising the isolated polynucleotide of claim 2.

4. The vector of claim 3, further comprising a genomic targeting sequence to hypoxanthine phosphoribosyltransferase (HPRT).

5. The isolated polynucleotide of claim 1, wherein said PITX3 regulatory element has at least 99% sequence identity to SEQ ID NO:2; and said PTIX3 basal promoter has at least 99% sequence identity to SEQ ID NO:3.

6. An isolated polynucleotide comprising the sequence of SEQ ID NO:1.

7. A method of expressing a sequence of interest in cells of the peripheral or central nervous system and progenitors thereof, the method comprising: (a) operably linking the sequence of interest to the polynucleotide of claim 1; and (b) introducing the polynucleotide of step (a) into cells of the peripheral or central nervous system and progenitors thereof.

* * * * *